(12) United States Patent
Van De Kerkhof et al.

(10) Patent No.: US 8,724,087 B2
(45) Date of Patent: May 13, 2014

(54) INSPECTION APPARATUS FOR LITHOGRAPHY

(75) Inventors: Marcus Adrianus Van De Kerkhof, Helmond (NL); Antoine Gaston Marie Kiers, Veldhoven (NL); Maurits Van Der Schaar, Eindhoven (NL); Leonardus Henricus Marie Verstappen, Weert (NL); Scott Anderson Middlebrooks, Duizel (NL); Andreas Fuchs, Meerbusch (DE)

(73) Assignee: ASML Netherlands B.V., Veldhoven (NL)

( * ) Notice: Subject to any disclaimer, the term of this patent is extended or adjusted under 35 U.S.C. 154(b) by 642 days.

(21) Appl. No.: 12/933,481

(22) PCT Filed: Apr. 8, 2009

(86) PCT No.: PCT/EP2009/002622
§ 371 (c)(1),
(2), (4) Date: Feb. 28, 2011

(87) PCT Pub. No.: WO2009/127355
PCT Pub. Date: Oct. 22, 2009

(65) Prior Publication Data
US 2011/0141444 A1 Jun. 16, 2011

Related U.S. Application Data

(60) Provisional application No. 61/071,155, filed on Apr. 15, 2008.

(51) Int. Cl.
*G03B 27/54* (2006.01)
(52) U.S. Cl.
USPC ............ 355/67; 355/53; 355/77; 356/369; 356/401; 356/446

(58) Field of Classification Search
USPC ............ 355/53, 67, 77; 356/369, 401, 446
See application file for complete search history.

(56) References Cited

U.S. PATENT DOCUMENTS 6,320,657 B1   11/2001   Aspnes et al.
6,850,333 B1   2/2005    Stanke et al.
(Continued)

FOREIGN PATENT DOCUMENTS

EP   1 628 164 A2        2/2006
WO   WO 02/29374 A1      4/2002

OTHER PUBLICATIONS

International Search Report mailed Jun. 23, 2009 for International Application No. PCT/EP2009/002622, 5 pgs.

(Continued)

*Primary Examiner* — Steven H Whitesell Gordon
*Assistant Examiner* — Mesfin T Asfaw
(74) *Attorney, Agent, or Firm* — Sterne, Kessler, Goldstein & Fox P.L.L.C.

(57) ABSTRACT

A scatterometer configured to measure a property of a substrate, includes a radiation source configured to provide a radiation beam; and a detector configured to detect a spectrum of the radiation beam reflected from a target (30) on the surface of the substrate (W) and to produce a measurement signal representative of the spectrum. The apparatus includes a beam shaper (51, 53) interposed in the radiation path between the radiation source and the detector, the beam shaper being configured to adjust the cross section of the beam dependent on the shape and/or size of the target.

19 Claims, 9 Drawing Sheets

(56) References Cited

U.S. PATENT DOCUMENTS

2002/0039184 A1* 4/2002 Sandusky ............... 356/369
2004/0090626 A1   5/2004 Wielsch et al.
2006/0066855 A1* 3/2006 Boef et al. ............... 356/401

OTHER PUBLICATIONS

International Preliminary Report on Patentability and Written Opinion of the International Searching Authority directed to related International Patent Application No. PCT/EP2009/002622, mailed Oct. 19, 2010; 7 pages.

* cited by examiner

INSPECTION APPARATUS FOR LITHOGRAPHY

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. This measurement may take place during the lithographic process, or separately from it, but is usually carried out using a separate metrology apparatus from the lithographic apparatus. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Overlay may be measured using angularly resolve scatterometry as overlay errors, that is an offset of a structure on one substrate layer with respect to a structure on a lower layer, give rise to an asymmetry in the angular scatter spectrum. This is generally measured using targets or marks, in the form of overlaid gratings or periodic structures, which may be placed in the scribe lanes just outside of the chips that are being made. However, the size and shape of the beam may not match the target. This is undesirable where there are several alignment targets of varying sizes and shapes within the scribe lines, as cross-talk may occur between the signals from neighbouring alignment targets.

U.S. Pat. No. 6,850,333 discloses a metrology instrument for measuring a grating-like target on a sample. An asymmetric elongated shape aperture is used to shape the radiation beam such that the measurement spot extends over many grating lines, but stays confined within the grating region. However, such an arrangement may not be flexible.

SUMMARY

It is desirable to provide a scatterometer in which it is possible to adjust the size and shape of the radiation beam incident on the target.

According to an aspect of the invention, there is provided a scatterometer configured to measure a property of a substrate, including a radiation source configured to provide a radiation beam; a detector configured to detect a spectrum of the radiation beam reflected from a target on the surface of the substrate and to produce a measurement signal representative of the spectrum; and a beam shaper interposed in the radiation path between the radiation source and the detector, the beam shaper being configured to adjust the cross section of the beam dependent on the configuration of the target.

According to an aspect of the invention, there is provided a method of measuring a property of a substrate, including generating a radiation beam with a source; detecting a spectrum of the radiation beam reflected from a target on the surface of the substrate and producing a measurement signal representative of the spectrum; and shaping the radiation beam, prior to said detecting, to adjust the cross section of the beam dependent on the configuration of the target.

According to an aspect of the invention, there is provided a method of measuring a property of a substrate, including providing a radiation beam; detecting a spectrum of the radiation beam reflected from a target on the surface of the substrate and producing a measurement signal representative of the spectrum; and trimming the reflected radiation after reflection from the target.

According to an aspect of the invention, there is provided a device manufacturing method including forming a pattern on a substrate; determining a value related to a parameter of the pattern, the determining including generating a radiation beam; detecting a spectrum of the radiation beam reflected from a target on the surface of the substrate and producing a measurement signal representative of the spectrum; shaping the radiation beam, prior to said detecting, to adjust the cross section of the beam dependent on the configuration of the target.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
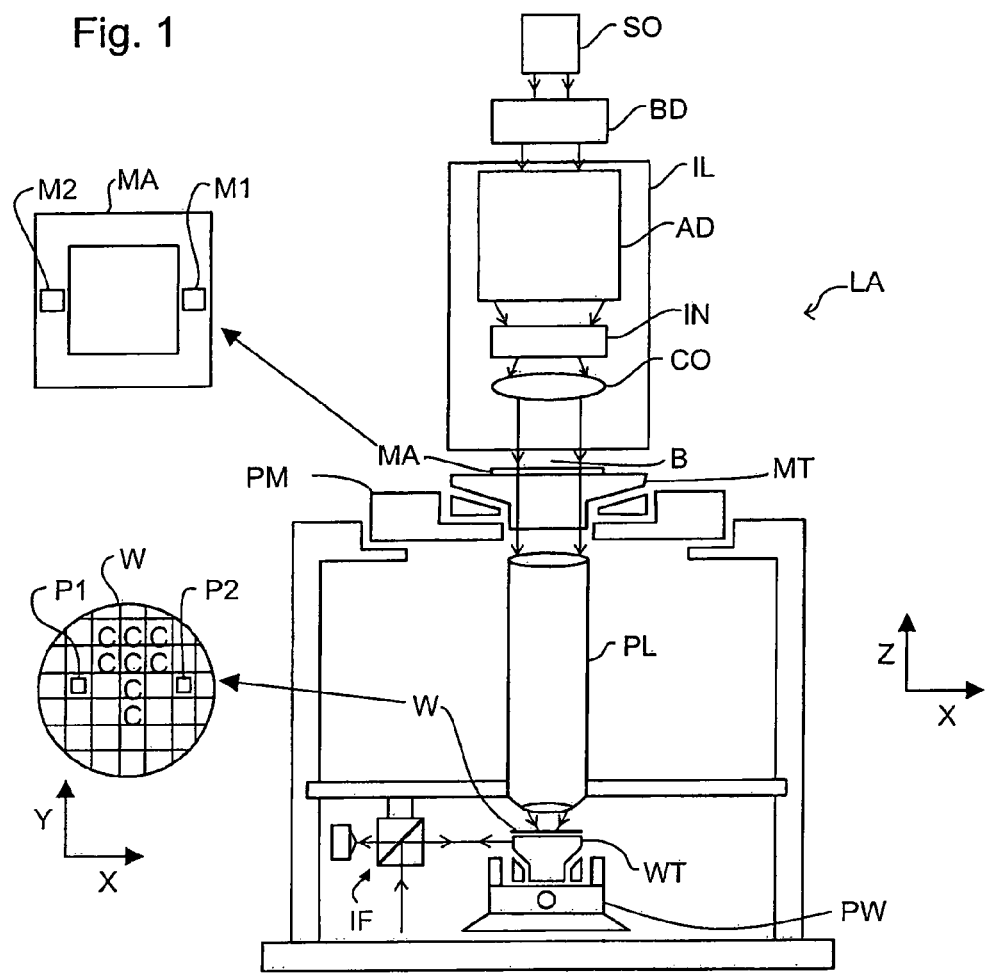
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation); a patterning device support or support structure (e.g. a mask table) MT constructed to support a patterning device (e.g. a mask) MA and connected to a first positioner PM configured to accurately position the patterning device in accordance with certain parameters; a substrate table or substrate support (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
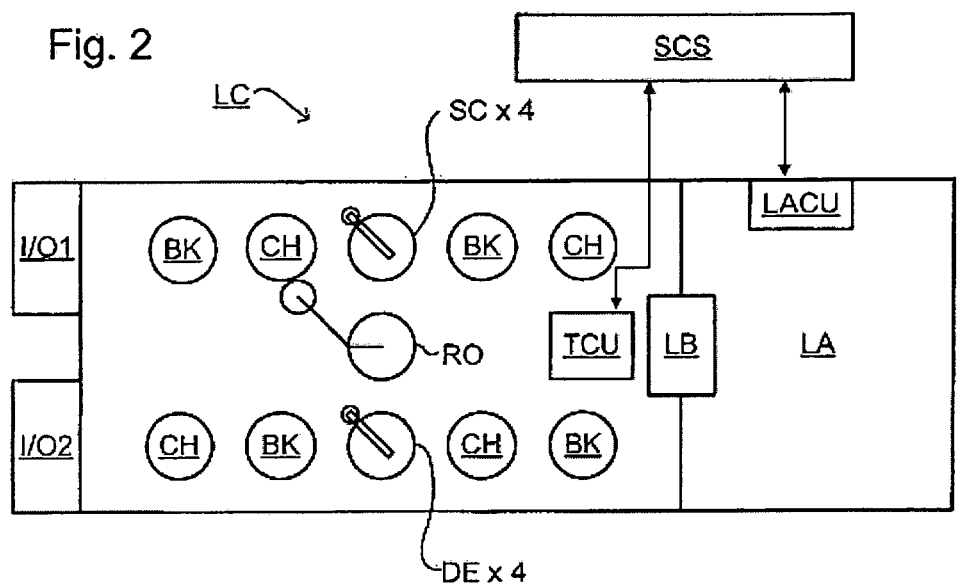
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
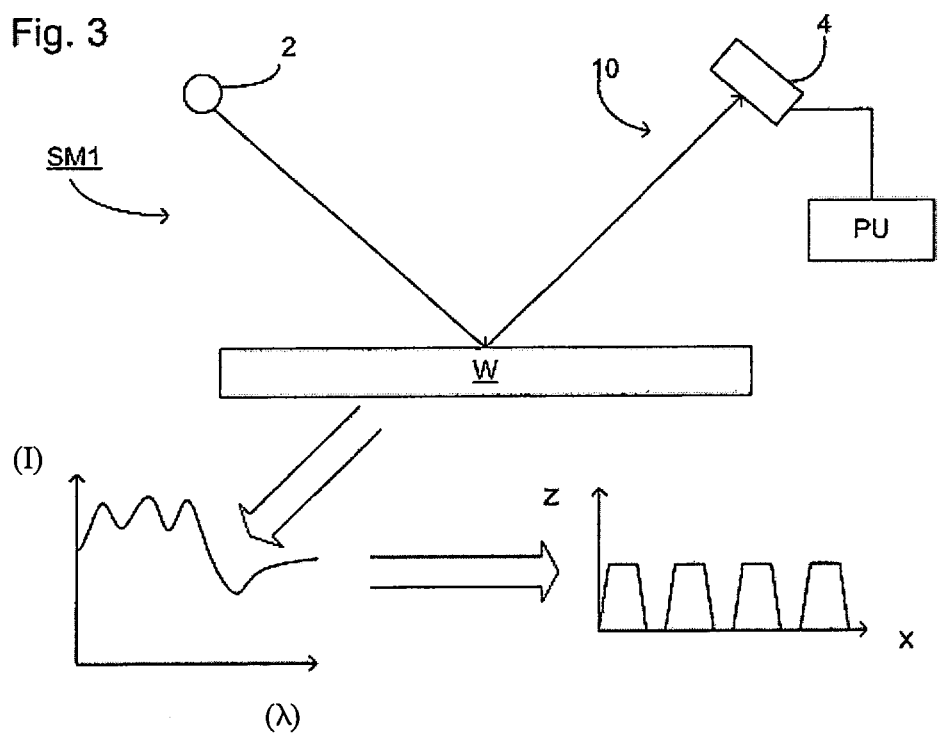
FIG. 3 depicts a scatterometer in accordance with an embodiment of the invention.

FIG. 3 depicts a scatterometer SM1 which may be used in an embodiment of the present invention. It includes a broadband (white light) radiation projector 2 which projects radiation onto a substrate W. The reflected radiation is passed to a spectrometer detector 4, which measures a spectrum 10 (intensity (I) as a function of wavelength ($\lambda$)) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
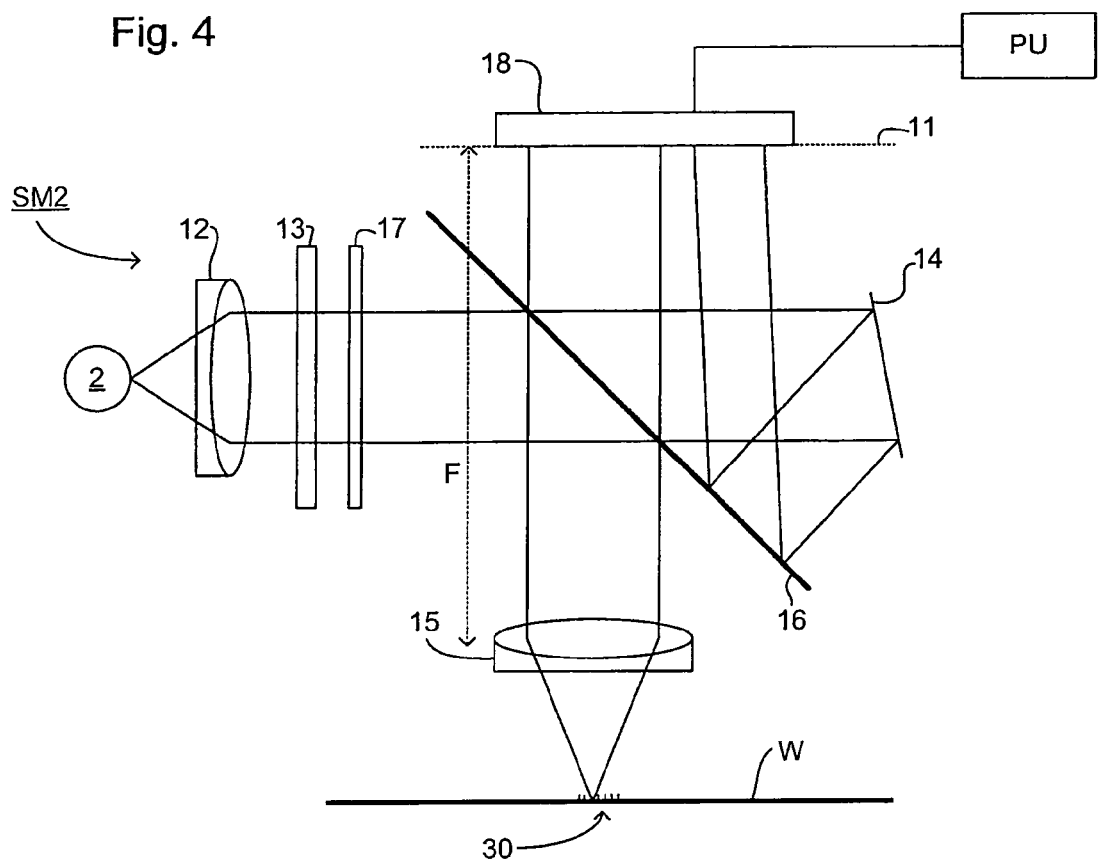
FIG. 4 depicts a scatterometer in accordance with an embodiment of the invention.

Another scatterometer SM2 that may be used with an embodiment of the present invention is shown in FIG. 4. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband radiation or light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least $2\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes. In the case of overlay metrology, as discussed above, the target will take the form of two overlaid gratings.

Figure 5:
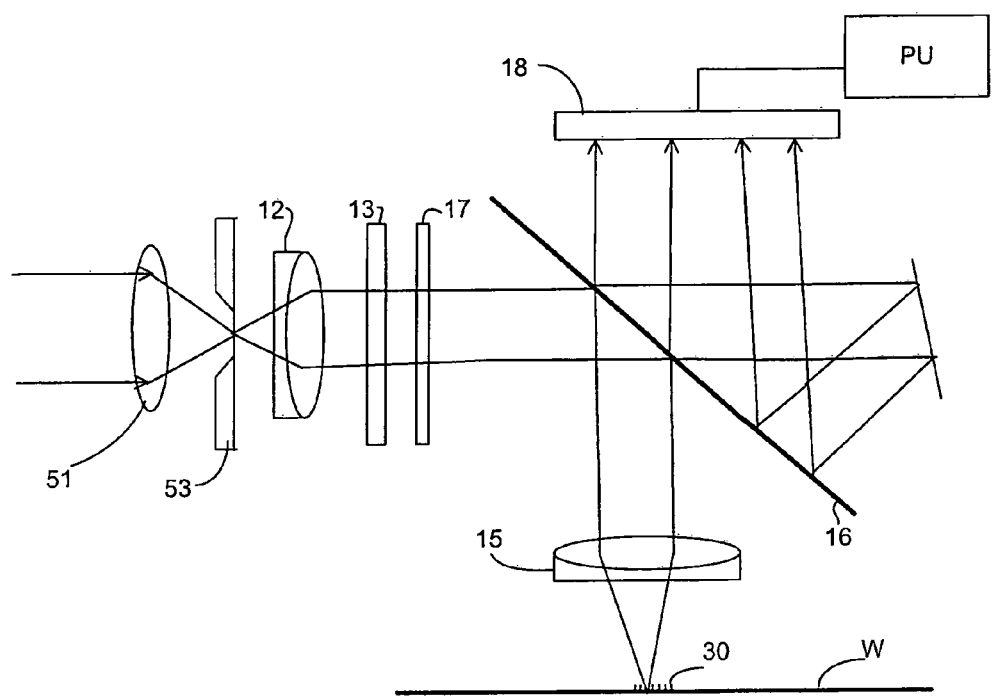
FIG. 5 depicts a scatterometer in accordance with an embodiment of the invention.

Referring now to FIGS. 5 to 11, in accordance with an embodiment of the invention the size of a measurement spot produced by the radiation beam on the grating 30 is adjusted, dependent on the configuration of the grating, using a beam shaping arrangement or beam shaper interposed in the radiation path between the radiation source and the target. FIG. 5 is an adaptation of the scatterometer shown in FIG. 4, but includes a beam shaper including a lens 51 and an aperture 53.

As indicated in FIG. 5, the radiation source (not shown in FIG. 5) is arranged to produce a parallel beam of relatively large cross section, in comparison to the area of the grating 30, the beam then passing through the beam shaper which is arranged at a position conjugate to the pupil plane. The beam shaper is effective to restrict the size of the radiation beam which is focused by lens 15 onto the target 30, so as to produce a smaller measurement spot than would have been produced if the beam had not passed through the beam shaper 51,53.

Figure 6:
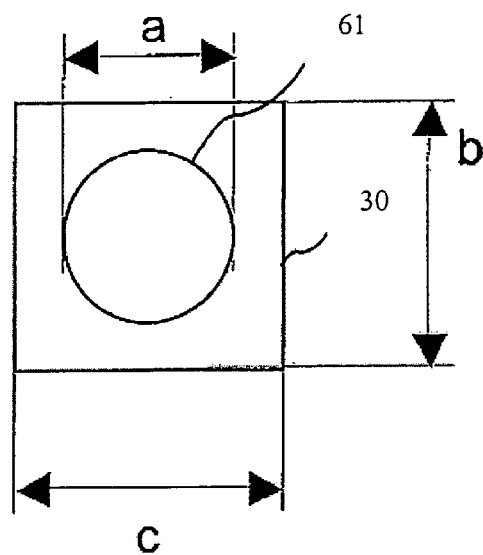
FIG. 6 illustrates a typical measurement spot positioned on a grating.
Figure 7:
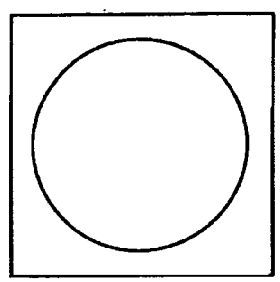
FIGS. 7 and 8 show measurement spots on a grating produced by a scatterometer in accordance with an embodiment of the invention.
Figure 8:
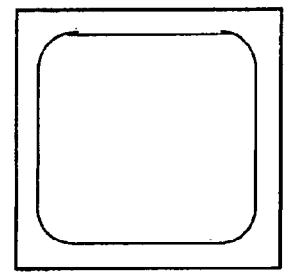
Figure 9:
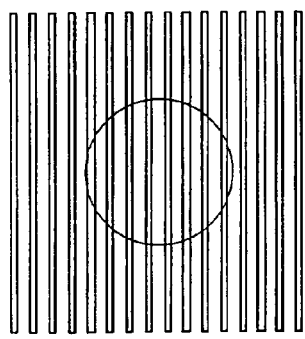
FIGS. 9 and 10 show the effect of a change in measurement spot size on the coverage of a grating.
Figure 10:
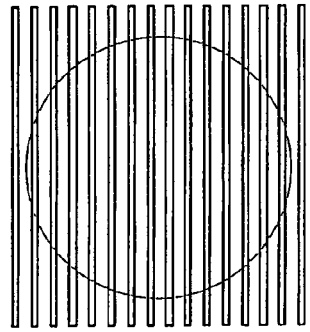

The effect of the smaller measurement spot can be seen by reference to FIGS. 6 to 11. As illustrated in FIG. 6, a typical value for the diameter of the measurement spot 61 as produced by the radiation source for use with a target in the form of a grating, that is parameter a in FIG. 6, will be 95 μm. A typical size for the grating 30, that is parameters b and c, will be 40×40 μm. Thus, the area illuminated by the measurement spot will be 30% of the total area. However if it is possible to increase the spot size as indicated in FIG. 7 a filling factor of about 70% can be achieved. Alternatively if a squarer spot is produced of the shape shown in FIG. 8, a filling factor of about 90% can be achieved. Furthermore, as indicated in FIGS. 9 and 10 if the size of the spot is increased relative to the size of the grating, further grating lines can be illuminated, giving rise to a signal more representative of the whole grating. Thus, adapting the size and shape of the measurement spot may give rise to a higher quality measurement signal.

Optimization of the size of the beam relative to the grating 30, can be achieved dynamically by altering the size of the aperture in the beam shaper. This can be achieved by using a wheel having different aperture openings, the choice of aperture opening being dependent on the size and shape of the grating. An iris type aperture may also be used. Alternatively an adjustable aperture such as a liquid crystal device may be used to adjust the size of the aperture. In such a dynamic measurement technique, the aperture is matched to the grating to achieve maximum sensitivity to alignment, the alignment being measured and corrected.

Details of beam shapers which may be used in a scatterometer in accordance with an embodiment of the invention are described in copending application U.S. Patent Application Ser. No. 61/009,192, the contents of which are hereby incorporated by reference.

Figure 11:
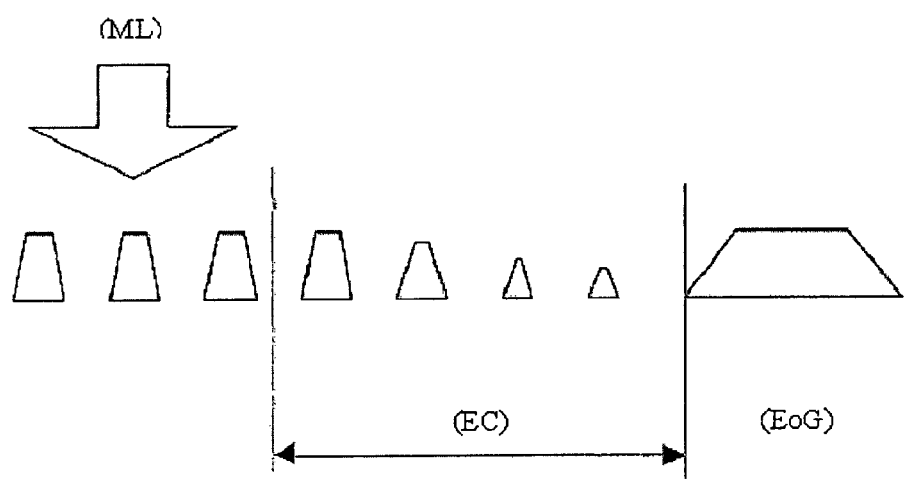
FIG. 11 illustrates the effect of the position of the measurement spot on the grating.

Turning now to FIG. 11, the inventors for the present application have found that if the measurement spot or measurement light (ML) reaches the edge of the grating (EoG), the quality of the pattern produced may be poor due to anomalies in the grating structure near the edge of the grating (edge clearance (EC)). Thus, the signal to noise ratio of the signal will depend on the alignment of the measurement spot on the grating. Variation of the measurement spot size on the grating may itself give rise to misalignment of the spot position and the grating. The position of the wafer W may be adjusted during the dynamic measurement, so as to avoid signals originating from radiation which has been diffracted from the edge of the grating 30.

Figure 12:
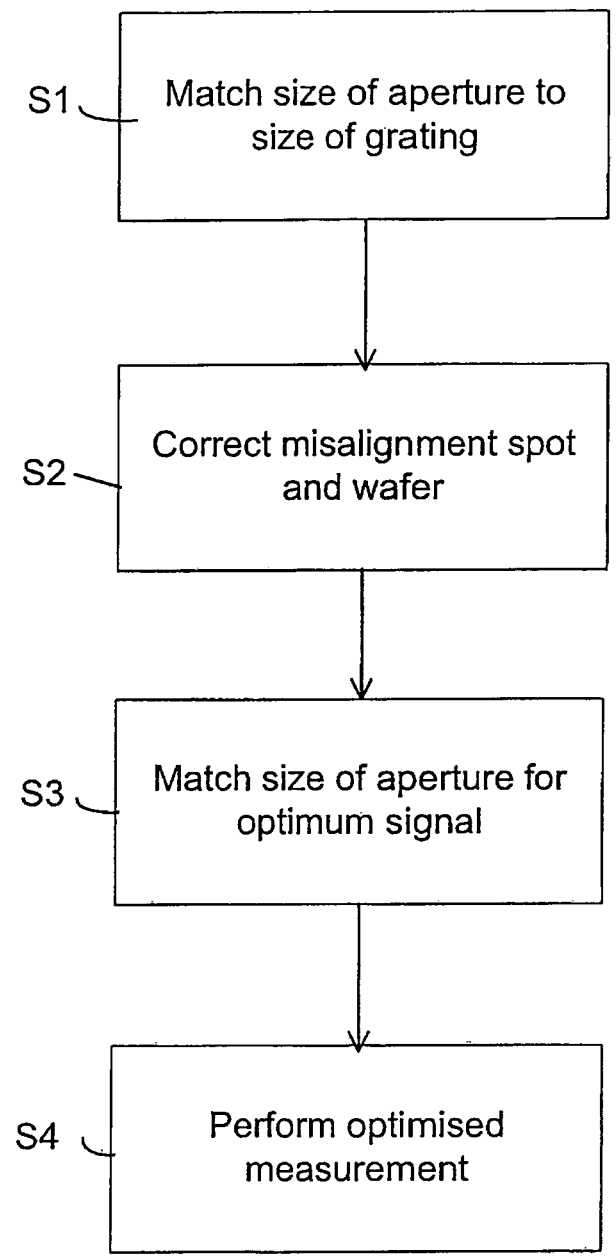
FIG. 12 illustrates a method of aligning the measurement spot and grating.

Alignment of the measurement spot and grating may be performed using the method shown in FIG. 12. In procedure S1, the size of the aperture is matched to the size of the grating to achieve maximum sensitivity to the alignment. The misalignment of the wafer W and the measurement spot is then measured and corrected in procedure S2. The size of the aperture is then matched to the grating for an optimum signal, depth of focus and minimized sensitivity to the alignment of the wafer W in procedure S3. Finally, the optimized measurements are performed in procedure S4.

In an embodiment, a signal adjuster is configured to adjust the measurement signal to compensate for an alignment of the radiation beam and the target. Further, a position adjuster may be used to adjust the relative positions of the radiation beam and the target in order to optimize the measurement signal.

Alternatively the processing unit PU, can be arranged to correct the measured signal mathematically as a function of the measurement spot size and the position of the measurement spot on the grating.

Figure 13:
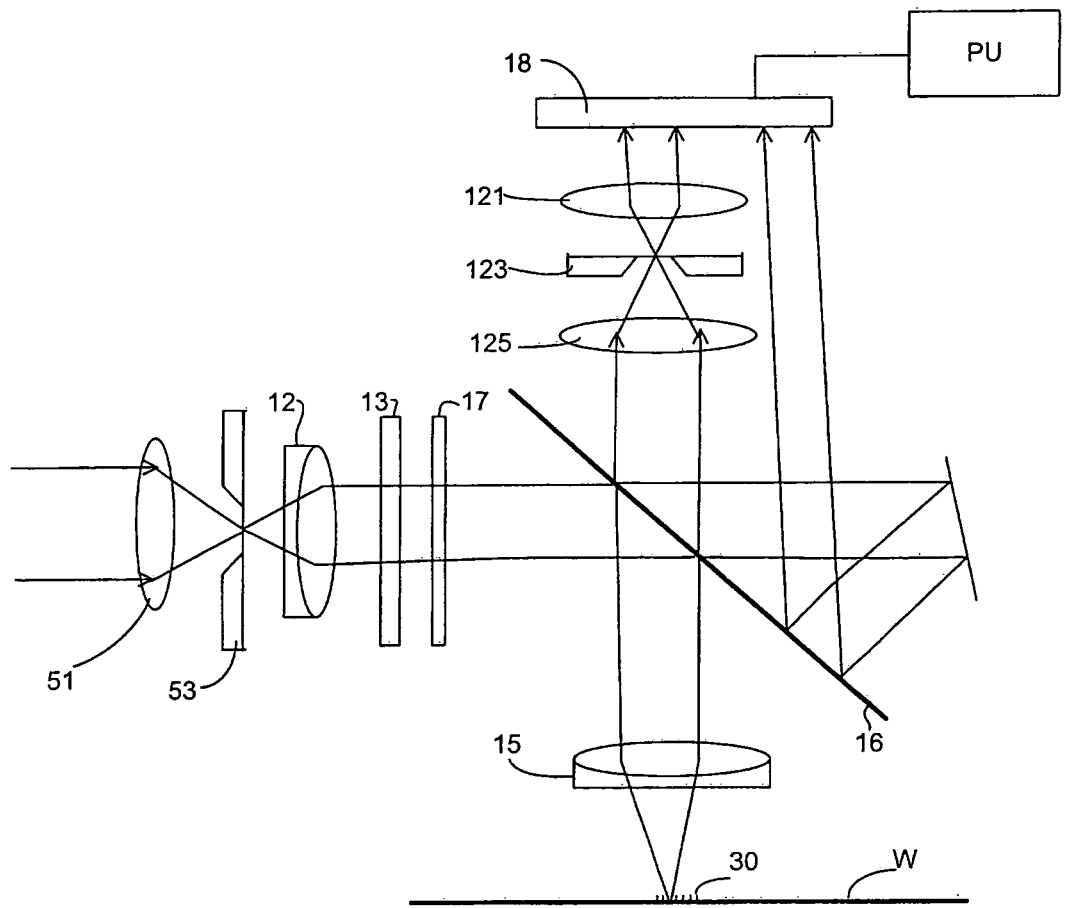
FIG. 13 illustrates a scatterometer in accordance with an embodiment of the invention.

Turning now to FIG. 13, which illustrates an embodiment of the invention, it may be desirable to provide a second beam shaper between the target and the detector at a position conjugate to the image plane. As the target may sometimes be overfilled with the radiation beam, the useful or central information can thus be subsequently selected by the second beam shaper. Alternatively, the second beam shaper may be used to compensate for misalignment of the measurement beam on the grating 30.

In FIG. 13, the second beam shaper is shown as an aperture 123, which may be variable as in the first beam shaper discussed in relation to the embodiment of FIG. 5, together with lens arrangement 121, 125 effective to focus the diffraction pattern on the detector 18.

Figure 14:
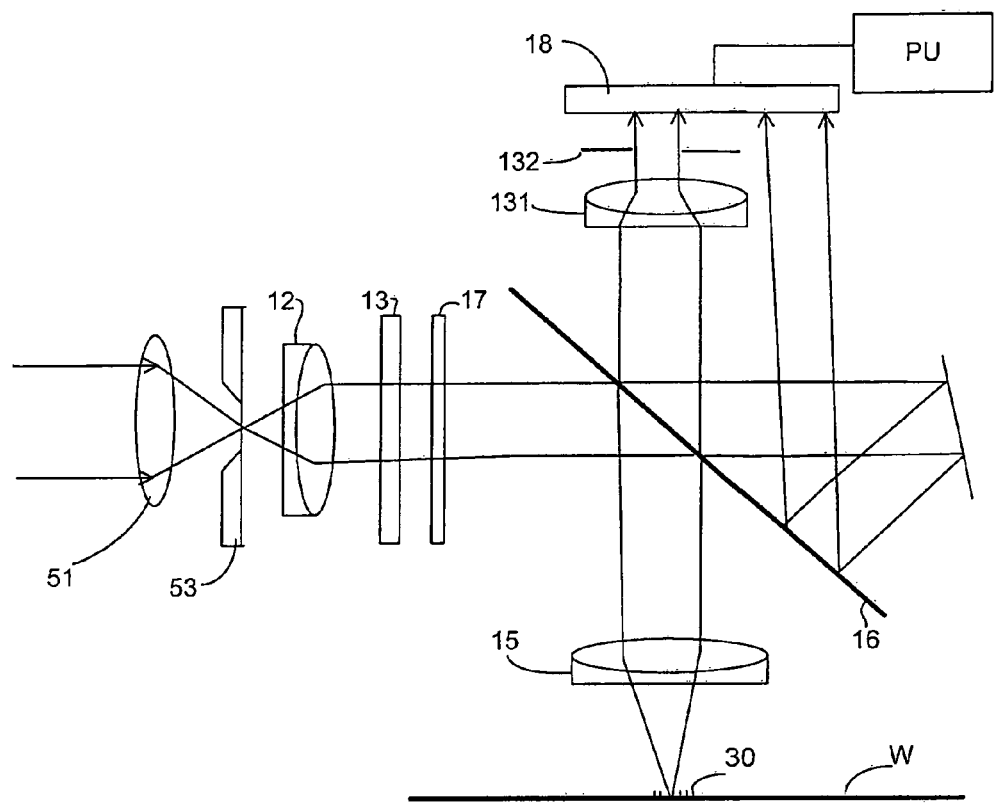
FIG. 14 depicts a scatterometer in accordance with an embodiment of the invention.

Turning now to the embodiment of FIG. 14, the second beam shaper takes the form of an adjustable zoom lens 131 which images the beam reflected from the target onto a fixed aperture 133 so as to vary the image size on the detector 18.

It will be appreciated that in the embodiments illustrated in FIGS. 13 and 14, beam shaper are included at both the upstream position at a position conjugate to the pupil plane and at the downstream position at a position conjugate to the image plane. It may be beneficial in some cases however to only have a beam shaper at the downstream position, that is at a position conjugate to the image plane. Such an arrangement will be effective to trim the edges of the diffraction pattern produced by the measurement spot produced by the source 2 shown in FIG. 4 in the absence of the first beam shaper. Such an arrangement may be used to address any misalignment of the beam and target and to avoid signals arising from the outer edge of the grating as discussed above.

It will also be appreciated that a downstream beam shaper will be of benefit in situations, other than when the second beam shaper is designed to take account of the configuration of the target.

It will also be appreciated that the first beam shaper may be arranged to have two or more apertures, such that a corresponding number of targets formed on the wafer W may be illuminated simultaneously by separate beams. In such an arrangement, a further beam splitter may be needed to split the reflected beams to enable their detection by detector 18.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A scatterometer configured to measure a property of a substrate, comprising:
   a radiation source configured to provide a radiation beam;
   a detector;
   a beam shaper interposed in a radiation path between the radiation source and the detector, the beam shaper being configured to adjust a cross section of the radiation beam based on a configuration of a target on a surface of the substrate and to output an adjusted radiation beam; and
   a controller configured to measure a misalignment between the adjusted radiation beam and the target and to compensate for the measured misalignment,
   wherein the detector is configured to detect a spectrum of the adjusted radiation beam reflected from the target and to produce a measurement signal representative of the spectrum.

2. The scatterometer according to claim 1, wherein the controller is configured to control a signal adjuster, the signal adjuster being configured to adjust the measurement signal to compensate for the measured misalignment.

3. The scatterometer according to claim 1, wherein the controller is configured to control a position adjuster, the position adjuster configured to adjust relative positions of the radiation beam and the target in order to optimize the measurement signal.

4. The scatterometer according to claim 1, wherein the beam shaper is interposed in a radiation path between the radiation source and the substrate.

5. The scatterometer according to claim 1, wherein the beam shaper is interposed in a radiation path between the substrate and the detector.

6. The scatterometer according to claim 1, wherein the beam shaper is configured to adjust the cross section of the radiation beam based on at least one of a shape of the target and a size of the target.

7. The scatterometer according to claim 1, wherein the beam shaper includes an aperture configured to selectively transmit a portion of the radiation beam as the adjusted radiation beam.

8. The scatterometer according to claim 1, wherein the beam shaper is configured such that the adjusted radiation beam is a variable cross section beam.

9. The scatterometer according to claim 1, wherein the beam shaper comprises an adjustable zoom lens.

10. The scatterometer according to claim 1, wherein the radiation source and the beam shaper are configured such that the target and another target on the substrate are illuminated substantially simultaneously.

11. The scatterometer according to claim 1, wherein the controller is configured to measure a reflection of the adjusted radiation beam from an edge of grating (EoG) portion of the target to measure the misalignment.

12. The scatterometer according to claim 1, further comprising a second beam shaper, wherein the controller is configured to control a second beam shaper to compensate for the measured misalignment.

13. The scatterometer according to claim 1, wherein the second beam shaper comprises a variable aperture.

14. A scatterometer configured to measure a property of a substrate, comprising:
   a radiation source configured to provide a radiation beam;
   a detector configured to detect a spectrum of the radiation beam reflected from a target on a surface of the substrate and to produce a measurement signal representative of the spectrum;
   a beam shaper interposed in the radiation path between the substrate and the detector, the beam shaper being configured to trim the reflected radiation beam after reflection from the target; and
   a controller configured to measure a misalignment between the radiation beam and the target and to compensate for the measured misalignment.

15. A method of measuring a property of a substrate, comprising:
   generating a radiation beam;
   detecting a spectrum of the radiation beam reflected from a target on the surface of the substrate;
   producing a measurement signal representative of the spectrum;
   shaping the radiation beam, prior to the detecting, to adjust a cross section of the radiation beam based on the configuration of the target;
   measuring a misalignment between the shaped radiation beam and the target; and
   compensating for the measured misalignment.

16. A method of measuring a property of a substrate, comprising:
   generating a radiation beam;
   detecting a spectrum of the radiation beam reflected from a target on a surface of the substrate;
   producing a measurement signal representative of the spectrum;
   trimming the reflected radiation after reflection from the target;
   measuring a misalignment between the radiation beam and the target; and
   compensating for the measured misalignment.

17. A lithographic apparatus comprising:
   an illumination system arranged to illuminate a pattern;
   a projection system arranged to project an image of the pattern on to a substrate; and
   a scatterometer configured to measure a property of the substrate, the scatterometer, comprising:
      a radiation source configured to provide a radiation beam;
      a detector;
      a beam shaper interposed in a radiation path between the radiation source and the detector, the beam shaper being configured to adjust a cross section of the radiation beam based on a configuration of a target on a surface of the substrate and to output an adjusted radiation beam wherein the detector is configured to detect a spectrum of the adjusted radiation beam reflected from the target and to produce a measurement signal representative of the spectrum; and
      a controller configured to measure a misalignment between the adjusted radiation beam and the target and to compensate for the measured misalignment.

18. A lithographic cell comprising:
   a coater arranged to coat a substrate with a radiation sensitive layer;
   a lithographic apparatus arranged to expose an image onto the radiation sensitive layer of the substrate coated by the coater;
   a developer arranged to develop the image exposed by the lithographic apparatus; and
   a scatterometer configured to measure a property of the substrate, the scatterometer, comprising:
      a radiation source configured to provide a radiation beam;
      a detector;

a beam shaper interposed in a radiation path between the radiation source and the detector, the beam shaper being configured to adjust a cross section of the radiation beam based on a configuration of a target on a surface of the substrate and to output an adjusted radiation beam, wherein the detector is configured to detect a spectrum of the adjusted radiation beam reflected from the target and to produce a measurement signal representative of the spectrum; and a controller configured to measure a misalignment between the radiation beam and the target and to compensate for the measured misalignment.

19. A device manufacturing method comprising:

forming a pattern on a substrate; and determining a value related to a parameter of the pattern, the determining including:

generating a radiation beam;

detecting a spectrum of the radiation beam reflected from a target on a surface of the substrate and producing a measurement signal representative of the spectrum;

shaping the radiation beam, prior to the detecting, to adjust a cross section of the radiation beam dependent on the configuration of the target;

measuring, a misalignment between the shaped radiation beam and the target; and compensating for the measured misalignment.

* * * * *